United States Patent
Eberle

(10) Patent No.: US 8,951,180 B2
(45) Date of Patent: Feb. 10, 2015

(54) CENTRIFUGE FOR SEPARATING OF WHOLE BLOOD INTO BLOOD COMPONENTS AS WELL AS FLUIDICALLY COMMUNICATING CONTAINERS FOR INSERTION INTO THE CENTRIFUGE, AS WELL AS A METHOD FOR OBTAINING A HIGHLY ENRICHED THROMBOCYTE CONCENTRATE OUT OF WHOLE BLOOD

(75) Inventor: Klaus-Günter Eberle, Tuttlingen (DE)

(73) Assignee: Andreas Hettich GmbH & Co. KG, Tuttlingen (DE)

( * ) Notice: Subject to any disclaimer, the term of this patent is extended or adjusted under 35 U.S.C. 154(b) by 245 days.

(21) Appl. No.: 12/875,399

(22) Filed: Sep. 3, 2010

(65) Prior Publication Data

US 2011/0059834 A1 Mar. 10, 2011

(30) Foreign Application Priority Data

Sep. 8, 2009 (DE) .......................... 10 2009 040 525

(51) Int. Cl.
*B04B 15/00* (2006.01)
*A61M 1/36* (2006.01)
(Continued)

(52) U.S. Cl.
CPC ............ *A61M 1/3693* (2013.01); *B01L 3/5021* (2013.01); *B01L 3/5635* (2013.01);
(Continued)

(58) Field of Classification Search
USPC ........ 494/2, 5, 7, 10, 16–18, 35, 42; 210/782; 422/72
See application file for complete search history.

(56) References Cited

U.S. PATENT DOCUMENTS 4,154,690 A 5/1979 Ballies
4,447,220 A 5/1984 Eberle
(Continued)

FOREIGN PATENT DOCUMENTS

DE 2946198 A1 5/1981
EP 1077733 A1 3/2006
(Continued)

OTHER PUBLICATIONS

European Patent Office, European Search Report, Application No./Patent No. 10175296.2-2316/ 2292334, Applicant Andreas Hettich GmbH & Co. KG, Mar. 22, 2012, Munich, Germany, pp. 1-3.
(Continued)

*Primary Examiner* — Timothy Cleveland
(74) *Attorney, Agent, or Firm* — Woodling, Krost and Rust

(57) ABSTRACT

The invention refers to a centrifuge for separating whole blood into its blood components and a method for extracting a highly enriched thrombocyte concentrate out of whole blood. For this purpose, the centrifuge comprises a closed loop and/or open-loop control unit as well as a drive unit coupled to the closed loop and/or open-loop control unit, a rotor (12) having at least two container receptacles (14a, 14b; 16a, 16) for removably holding containers (18, 20, 22, 24) being in fluid communication with each other, at least one sensor arranged between the container receptacles (14a, 14b; 16a, 16b) and coupled with the closed loop and/or open-loop control unit for detecting a separation layer. Herein, a motor/gear unit (30a, 30b, 32a, 32b) coupled to the closed loop and/or open-loop control unit is associated with each of the container receptacles (14a, 14b; 16a, 16b). Each of the motor/gear units is in operational contact through means (34) with each of the containers (18, 20, 22, 24) supported in the respective container receptacle (14a, 14b; 16a, 16b) such that a transfer and back-transfer of blood components between the containers (18, 20, 22, 24) is initiated.

5 Claims, 6 Drawing Sheets

(51) Int. Cl.
 *B01L 3/00* (2006.01)
 *B04B 5/04* (2006.01)
 *B04B 13/00* (2006.01)

(52) U.S. Cl.
 CPC .............. *B04B 5/0414* (2013.01); *B04B 13/00* (2013.01); *A61M 2202/0427* (2013.01); *A61M 2205/3306* (2013.01); *B04B 2005/0485* (2013.01); *B04B 2013/006* (2013.01)
 USPC ...................... 494/10; 494/7; 494/16; 494/35

(56) References Cited

U.S. PATENT DOCUMENTS

| | | | |
|---|---|---|---|
| 6,060,022 A * | 5/2000 | Pang et al. | 494/10 |
| 6,733,433 B1 * | 5/2004 | Fell | 435/2 |
| 7,285,085 B2 * | 10/2007 | Kim et al. | 494/20 |
| 7,364,657 B2 * | 4/2008 | Mandrusov et al. | 494/10 |
| 7,442,178 B2 | 10/2008 | Chammas | |
| 7,744,821 B2 | 6/2010 | Eberle | |
| 2002/0042336 A1 * | 4/2002 | Jorgensen et al. | 494/37 |
| 2002/0151423 A1 | 10/2002 | Jorgensen | |
| 2004/0082459 A1 * | 4/2004 | Min et al. | 494/45 |
| 2004/0167004 A1 | 8/2004 | Jorgensen et al. | |
| 2004/0182788 A1 | 9/2004 | Dorian et al. | |
| 2006/0062697 A1 | 3/2006 | Eberle | |
| 2006/0144803 A1 | 7/2006 | Eberle | |
| 2008/0286379 A1 * | 11/2008 | Wehling et al. | 210/787 |
| 2009/0209402 A1 | 8/2009 | Andersson | |

FOREIGN PATENT DOCUMENTS

| | | |
|---|---|---|
| EP | 1637172 B1 | 5/2008 |
| GB | 1592935 | 7/1981 |
| JP | 6-23037 | 2/1994 |
| JP | 2002-538900 | 11/2002 |
| WO | 0054825 A1 | 9/2000 |
| WO | 2007126357 A1 | 11/2007 |

OTHER PUBLICATIONS

German Patent and Trademark Office, Communication, Jun. 20, 2012, German Patent Application No. 102009040525.9, Applicant Andreas Hettich GmbH & Co. KG, Munich, Germany, pp. 1-8.

Japan Patent Office, Examination Report, Sep. 17, 2013, Application No. 2010-200267, pp. 1-5, Japan.

German Patent and Trademark Office Examination Report, German Serial No. 10 2009 040 525.9-23 Which Is the Priority Document, pp. 1-4, Mar. 19, 2010.

First Notification of Office Action, the State Intellectual Property Office of P. R. China, Patent Application Serial No. 201010277932.2, Applicant Andreas Hettich GmbH & Co. KG, Dec. 3, 2012, English Translation, pp. 1-9.

First Notification of Office Action, The State Intellectual Property Office of P. R. China, Patent Application Serial No. 201010277932.2, Applicant Andreas Hettich GmbH & Co. KG, Dec. 3, 2012, pp. 1-7.

* cited by examiner

CENTRIFUGE FOR SEPARATING OF WHOLE BLOOD INTO BLOOD COMPONENTS AS WELL AS FLUIDICALLY COMMUNICATING CONTAINERS FOR INSERTION INTO THE CENTRIFUGE, AS WELL AS A METHOD FOR OBTAINING A HIGHLY ENRICHED THROMBOCYTE CONCENTRATE OUT OF WHOLE BLOOD

This application claims priority to German patent application no. 10 2009 040 525.9-23 filed Sep. 8, 2009, which is incorporated herein in its entirety by reference hereto.

The invention refers to a centrifuge for separating whole blood into its blood components. The invention also refers to fluidically communicating containers for insertion into the centrifuge. The invention also refers to a method for obtaining a highly enriched thrombocyte concentrate out of whole blood by means of the centrifuge.

The extraction of a highly enriched thrombocyte concentrate out of whole blood is basically known. For this purpose, the whole blood is separated into erythrocytes having a high density and thrombocytes or platelet rich plasma in a first centrifuge process by means of a centrifuge. An intermediate layer out of leukocytes forms a separation layer between the erythrocytes and the thrombocytes or platelet rich plasma, respectively. In a subsequent second centrifugation process, the thrombocyte or platelet rich plasma, respectively, is then separated into thrombocyte depleted plasma and the desired thrombocyte concentrate.

From EP 1 637 172 B1, a method for separating of blood components contained in bags is known. After separation of the whole blood into erythrocytes and thrombocyte rich blood plasma, it is basically possible with the disclosed apparatus to further process the thrombocyte rich blood plasma and, thereby, the extraction of thrombocyte concentrate. Besides a centrifuge for centrifugation, according to the teaching of EP 1 637 172 B1, a further apparatus is provided therein for squeezing-off. The required switching between centrifuge at the one hand and the squeezing-off device on the other hand, proves to be cumbersome and time consuming.

The invention is based on the objective to provide a centrifuge which allows a simplified production of a highly enriched thrombocyte concentrate.

According to the invention, the centrifuge for separating whole blood into its blood components comprises a closed loop and/or open-loop control unit as well as a drive unit coupled to the closed loop and/or open-loop control unit, a rotor having at least two container receptacles for removably supporting fluidically communicating containers, as well as at least one sensor arranged between the container receptacles and coupled to the closed loop and/or open-loop control unit for detecting a separation layer. Each motor/gear unit is coupled to the closed loop control unit and/or each motor/gear unit is coupled to an open-loop control unit. The closed loop control unit and/or the open loop control unit is/are associated with the container receptacles. The motor/gear units are in operational relationship with the containers supported in the respective container receptacles by means such that a transfer and back-transfer of blood components between the containers is initiated. In an advantageous manner, it is now possible by means of the inventive centrifuge to carry out an automatic transfer and back-transfer of blood components between the containers in the centrifuge. Since it is not necessary to remove one of the two containers, an undesired, subsequent intermixture is excluded such that the production of a highly enriched blood component, in particular the production of a highly enriched thrombocyte concentrate, is ensured. As already mentioned, since the containers remain in the centrifuge during a transfer or a back-transfer, respectively, of blood components between the containers, there is additionally ensured a simplified handling, a shortened processing time as well as a reproducible extraction of thrombocyte concentrate having defined, high quality features.

According to a particularly advantageous embodiment of the invention, the rotor comprises at least two container receptacle pairs comprising two container receptacles each for removably supporting two containers each being in fluid communication with each other, wherein a sensor for detecting a separation layer is arranged between each container receptacle pair. The container receptacle pairs are closed systems for the sterile processing of blood samples. The pairwise arrangement of two containers proves to be advantageous since optimal loading and smooth operation of the centrifuge optimal separation results.

Preferably, a further sensor is associated with each container receptacle pair. The sensor can detect if the proper container receptacle type is being used. Providing the further sensor has the positive effect that improper container receptacles may be in use and, thereby, an unbalance may be detected ahead of time.

In order to ensure a cost-effective and reliable detection of the separation layer or the type of equipment being used in a container receptacle pair, respectively, the sensors are embodied as optical sensors.

For ensuring a low-noise data- and energy transfer, the centrifuge comprises an inductive interface for an inductive transfer of data and energy.

The invention is furthermore based on the object to provide fluidically communicating containers in the centrifuge which ensure good efficiency and simplified handling.

According to the invention, the fluidically communicating containers form a closed system for the sterile processing of blood samples, and the containers are each formed in the shape of a tubule having a piston moveably arranged in the interior of the tubule, wherein the tubules are in operational connection with the motor/gear unit associated with the respective container receptacle, by a push rod being in removable contact with the piston. The arrangement of the container according to the invention proves to be particularly advantageous since the tubules do not comprise sediment nests because of their strong structure, and, thereby, good efficiency is ensured. Since the pistons are arranged in the tubules, the coupling, by means of the push rod with the related motor/gear unit of the centrifuge enables simple handling.

According to a particularly advantageous embodiment of the invention, at least in one of the tubules, the piston is formed in two parts comprising, as seen in the inward movement direction of the piston, a forward piston portion and a rearward piston portion. Therein, the forward and rearward piston portion are removably connected to each other, and the rearward piston portion comprises a through bore closed by a seal such that, by disconnecting the two piston portions, the forward piston portion may be moved relative to the rearward piston portion by means of a piston rod insertable through the through bore in the rearward piston portion. The two-part arrangement of the piston proves to be particularly advantageous since, thereby, a targeted intermixture of the blood component contained in this area of the tubule is possible by means of an upwards and downwards movement of the forward piston portion.

Therein, the rearward and forward piston portion are preferably removably connected to each other by means of a bayonet coupling, and the forward piston portion comprises a bore with an interior thread, and the piston rod comprises, in its forward portion, an outer thread formed correspondingly thereto. The arrangement of the removable connection by means of a bayonet coupling as well as the provision of a screw connection between the piston rod and the forward piston portion proves to be particular advantageous since the bayonet coupling as well as the threading between the piston rod and the forward piston portion may be operated by means of a turning movement. For example, the piston rod may be connected to the forward piston portion by means of a rotation in the clockwise direction, whereas—after the piston rod is fixedly connected to the forward piston portion—a subsequent rotation in the anti-clockwise direction effects disconnection of the bayonet coupling.

In order to ensure an effective detection of the separation layer by means of the optical sensor, the two tubules are connected in fluid communication with each other by means of a transparent hose.

According to a further embodiment, two or more tubules are connected in fluid communication with each other by means of a transparent hose which is divided up by a coupling element into two or more hose lines each having a check valve. For example, if one tubule is filled with whole blood and fluidically connected with two further tubules by means of a hose comprising a coupling element, besides the separation of the whole blood into its blood components also a transfer of the separated blood components into two separate tubules is made possible now in an advantageous way.

Preferably, the hose comprises an integrated valve. The integration of the valve has the effect that an undesired backflow is prohibited thereby during the centrifugation or after a centrifugation process, respectively.

According to a further advantageous embodiment of the invention, the hose comprises, at its end, connection elements by which the hose is adapted to be removably connected through the closure caps of the tubules. Provision of the connection elements proves to be advantageous since handling is made simple.

The invention is furthermore based on the object to provide a method for extracting a highly enriched thrombocyte concentrate out of whole blood.

The method of the invention comprises the following steps:
Inserting at least two tubules fluidically connected to each other by a hose, into the container receptacles where the first tubule contains the whole blood and the second tubule, named secondary tubule in the following, contains a biocompatible material if needed;
Providing an operational connection between the pistons located in the tubules, and the related motor/gear units by means of a push rod;
Initiating movement of the centrifuge with a first centrifuge speed;
First centrifugation until an erythrocyte concentrate having a high density as well as a thrombocyte enriched blood plasma separated there from by a separation layer have formed in the first tubule;
Reducing the centrifuge speed to a first squeezing-off speed;
Starting movement of the motor/gear unit associated with the first tubule and being in operational connection with the piston, and squeezing-off the thrombocyte enriched blood plasma through the hose into the secondary tubule until the sensor has detected the separation layer;
Increasing the speed to a second centrifuge speed;
Second centrifugation until a thrombocyte concentrate with higher density as well as separated thrombocyte depleted blood plasma have formed in the secondary tubule;
Reducing the centrifuge speed to a second squeezing-off speed;
Starting movement of the motor/gear unit associated with the secondary tubule and being in operational connection with the piston, and squeezing back the thrombocyte depleted blood plasma into the first tubule;
Breaking down the centrifuge;
Slowing down the motor/gear units;
Removing the tubules.

Since, according to the method of the invention, the thrombocyte depleted blood plasma is removed prior to removing the secondary tubule out of the secondary tubule receptacle, the repeated intermixing is excluded such that, in an advantageous way, a highly enriched thrombocyte concentrate can be produced by means of the method of the invention.

Preferably, all method steps are automated, i.e. carried out according to a prior defined running scheme, except the steps of inserting and removing the tubules. Since the parameters for the first centrifugation (time, speed or RCF/radius, speeding up and breaking down ramps), the first squeezing-off speed, the parameter for the second centrifugation (time, speed or RCF/radius, speeding up and breaking down ramps), the second squeezing-off speed, the back squeezing volume on the back squeezing process as well as the breaking down ramp for breaking down the centrifuge are carried out according to a pre-defined running scheme, faulty operation by the operators is almost excluded.

Therein, the above-mentioned parameters may be input, with the centrifuge in still stand, in a comfortable way by the operators into the closed loop and/or open-loop control unit or may be changed or may be adapted to the respective application, respectively.

In particular for the case that the secondary tubule has a biocompatible material contained therein, according to a particularly advantageous embodiment of the method for producing the thrombocyte concentrate, the secondary tubule is used having a two-part piston, and, after removing the secondary tubule from the centrifuge, the contents of the secondary tubule, i.e. the biocompatible material and the thrombocyte concentrate, are mixed by means of the forward piston portion. This has the effect that, if the application requires this, a homogenous paste out of thrombocyte concentrate and biocompatible material can be obtained for filling up defects. This is subsequently applied into the defect.

Further advantageous features and application possibilities of the present invention result from the following specification in connection with the embodiment shown in the drawing.

In the following, the invention is described with reference to the embodiment shown in the drawing, in the specification, in the claims and the drawing the terms contained in the list of reference signs given below and the related reference signs are used. In the drawings:

BRIEF DESCRIPTION OF THE DRAWINGS

In the following specification and in the figures, the same parts and components are characterized by the same reference signs for avoiding repetition as far as no further differentiation is necessary or makes sense.

DESCRIPTION OF THE INVENTION

Figure 1:
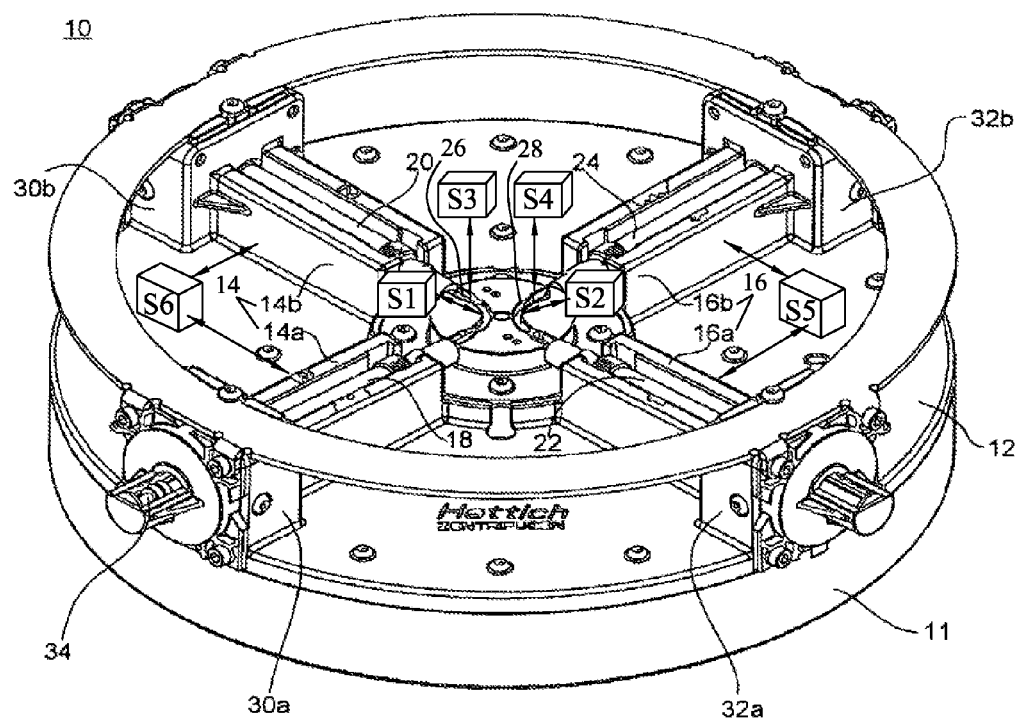
FIG. 1 is a perspective representation of a rotor having two container receptacle pairs within which two containers each in fluid communication with each other are contained.

FIG. 1 shows in a perspective view, a centrifuge all together provided with the reference number 10. Out of reasons of clarity, at present only a centrifuge head 11 and a rotor 12 is shown here assembled onto the centrifuge head 11. The associated closed loop and/or open-loop control unit as well as the drive unit for the centrifuge 10 are also not shown in the perspective view of FIG. 1 out of reasons of clarity, rather, they are schematically illustrated in FIG. 1A.

Figure 1A:
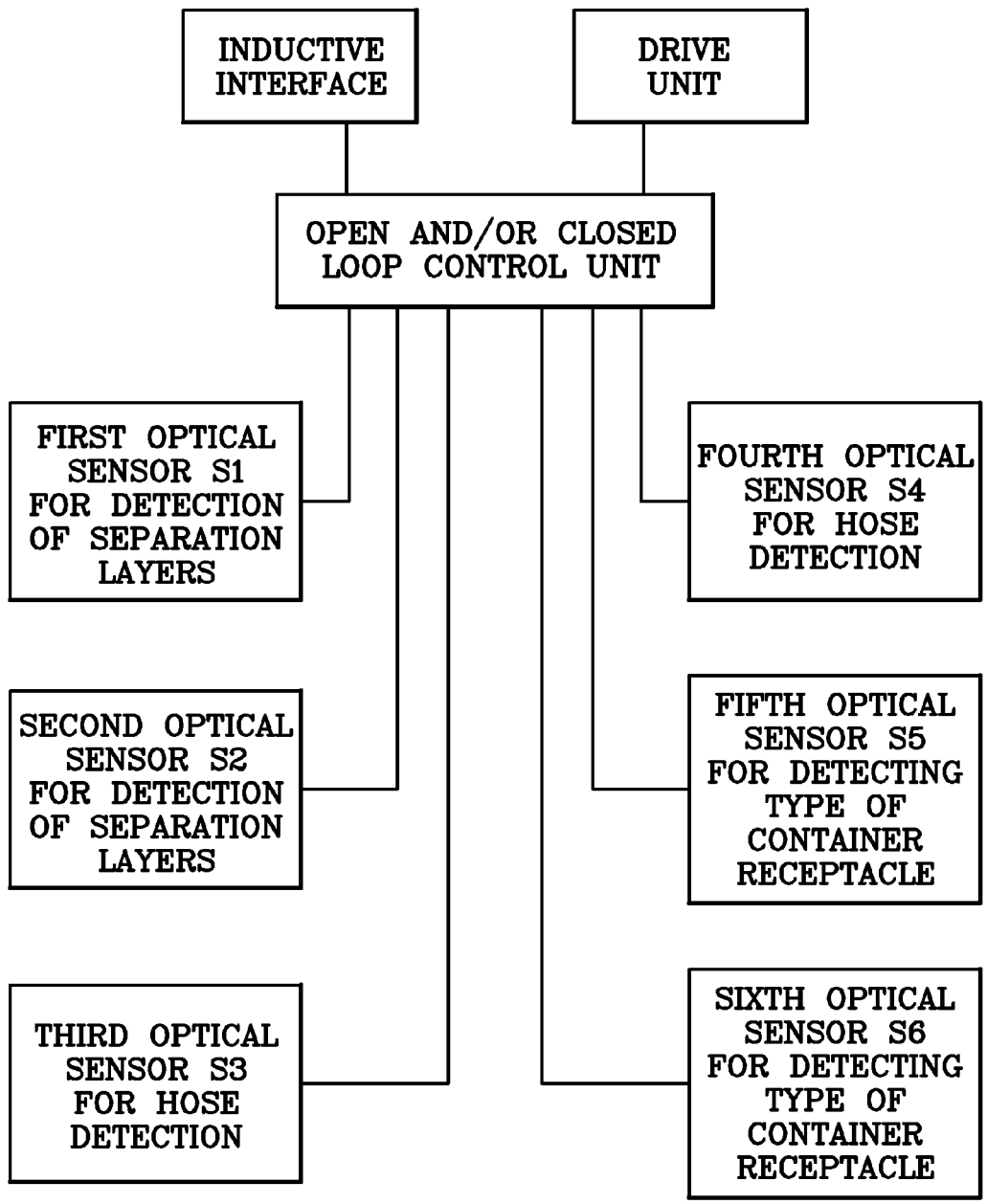
FIG. 1A is a diagrammatic view of the open and/or closed loop control unit, the first optical sensor, the second optical sensor, the third optical sensor, the fourth optical sensor, the fifth optical sensor, the sixth optical sensor, and the inductive interface and the drive unit.

FIG. 1A is a diagrammatic view of the open and/or closed loop control unit, the first optical sensor, the second optical sensor, the third optical sensor, the fourth optical sensor, the fifth optical sensor, the sixth optical sensor, and the inductive interface and the drive unit.

The rotor 12 comprises all together four container receptacles 14a, 14b as well as 16a, 16b. The two container receptacles 14a and 14b are named in the following simply as container receptacle pair 14, and the container receptacles 16a and 16b as container receptacle pair 16. Within each container receptacle pair 14, 16, there is contained a pair of containers each connected in fluid communication with each other in form of a tubule having a piston which is movably arranged in the interior of the tubule. For example, container receptacle pair 14 and, in particular, the container receptacle 14a includes tubule 18.

Receptacle pair 14 also includes container receptacle 14b which includes secondary tubule 20.

Accordingly, the container receptacle pair 16 comprises in the container receptacle 16a a tubule 22 and in the container receptacle 16b a secondary tubule 24. The tubules 18, 20 are connected to each other in fluid communication through a transparent hose 26 and form a closed system for the sterile processing of blood samples. The tubules 22, 24 are connected to each other in fluid communication through a transparent hose 28 and form a closed system for the sterile processing of blood samples.

As can be taken from FIG. 1, furthermore, the tubules 18, 20, 22, 24 are radially aligned, and the transparent hoses 26, 28 are guided in a central unit. Optical sensors S1, S2 for detecting a separation layer arising in the hose are associated with each hose 26, 28. First optical sensor S1 and second optical sensor S2 detect separation layers. Furthermore, the presence of a hose is monitored by means of optical sensors S3, S4 which are associated with each of the hoses 26, 28. Third optical sensor S3 and fourth optical sensor S4 detect the presence of hoses 26, 28. The sensors S1 and S2 are illustrated in FIG. 1 between respective pairs of container/tubule receptacles. S3 and S4 are illustrated in FIG. 1 between respective pairs of container/tubule receptacles.

Preferably, a fifth sensor S5 and a second sensor S6 are associated with each container receptacle pair. Sensors S5, S6 can detect if the proper container receptacle type is being used. Providing sensors S5, S6 has the positive effect that improper container receptacles may be in use and, thereby, an unbalance may be detected ahead of time.

As can be furthermore taken from FIG. 1, motor/gear units 30a, 30b, 32a, 32b are associated with respective container receptacles 14a, 14b, 16a, 16b disposed radially outwardly and are in operational connection by means of a push rod with the piston arranged in the respective tubule. Out of reasons of clarity only one push rod 34 is shown here at the motor/gear unit 30a.

Figure 2:
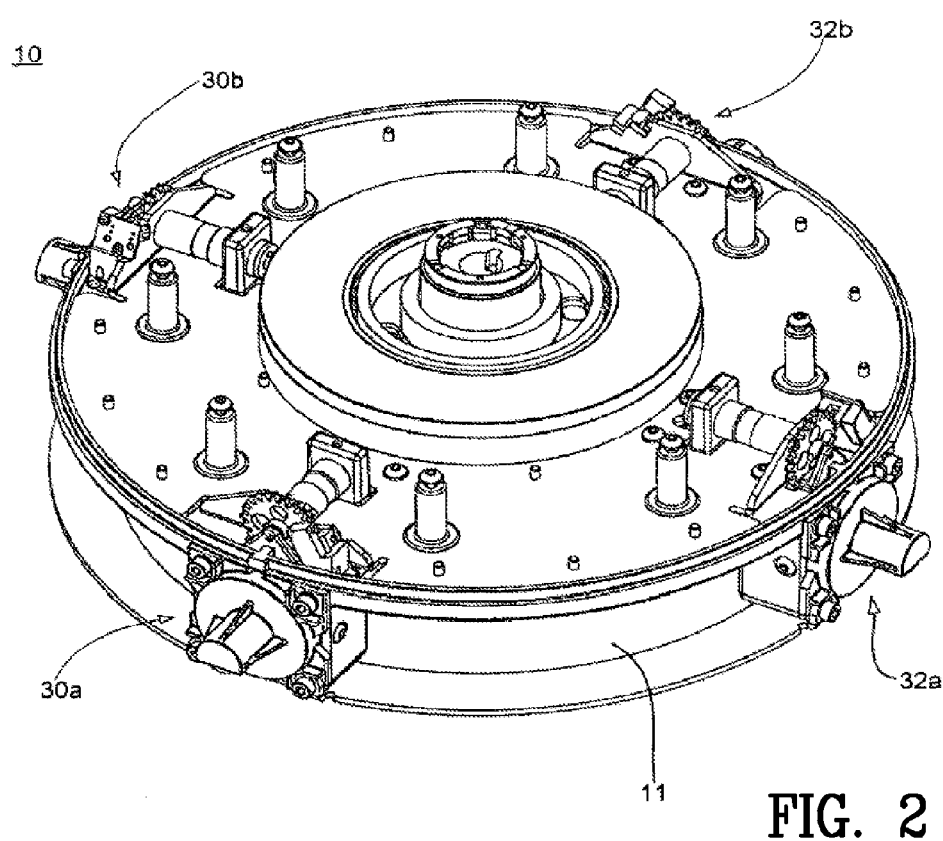
FIG. 2 is a perspective view of the centrifuge head of FIG. 1. without the rotor being attached.

FIG. 2 shows the rotor head 11 after removal of the rotor 12. Herein, the motor/gear units 30a, 30b, 32a, 32b are here shown again in detail.

Figure 3:
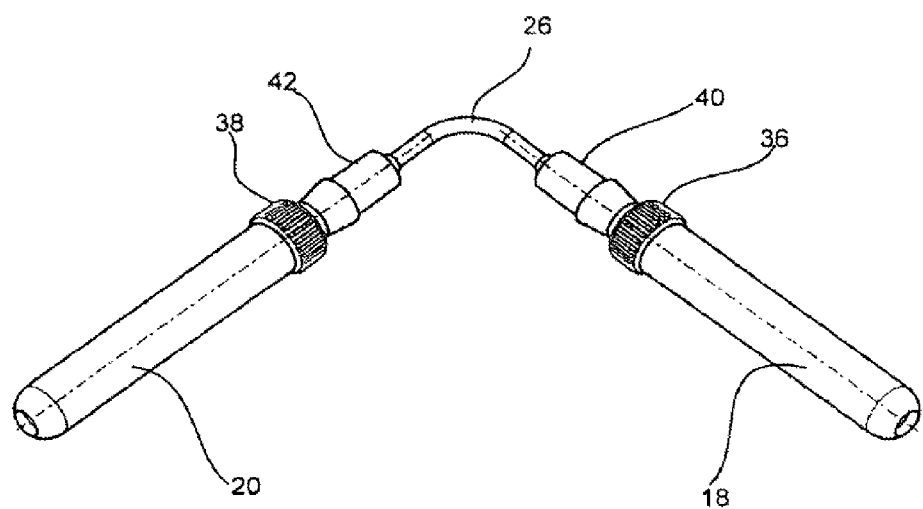
FIG. 3 is a perspective view of two tubules in fluidic communication with each other by means of insertion into the centrifuge.

FIG. 3 shows, in an enlarged presentation, the tubules 18 and 20 contained in the first container receptacle pair 14. As can be taken from FIG. 3, the tubules 18, 20 each comprise a removable closure cap 36, 38, while the transparent hose 26 is provided, at its ends, with connection elements 40, 42. By means of the respectively associated elements, closure cap/connection element 36/40 and/or 38/42, respectively, the fluid connection between the tubules 18, 20 can be established by means of the hose 26 in a simple manner. Whereas the tubule 18 serves for receiving the whole blood, the secondary tubule 20 is provided for receiving the separated blood component. The arrangement of the tubules 22, 24 contained in the second container receptacle pair 16 is accordingly.

Figure 4:
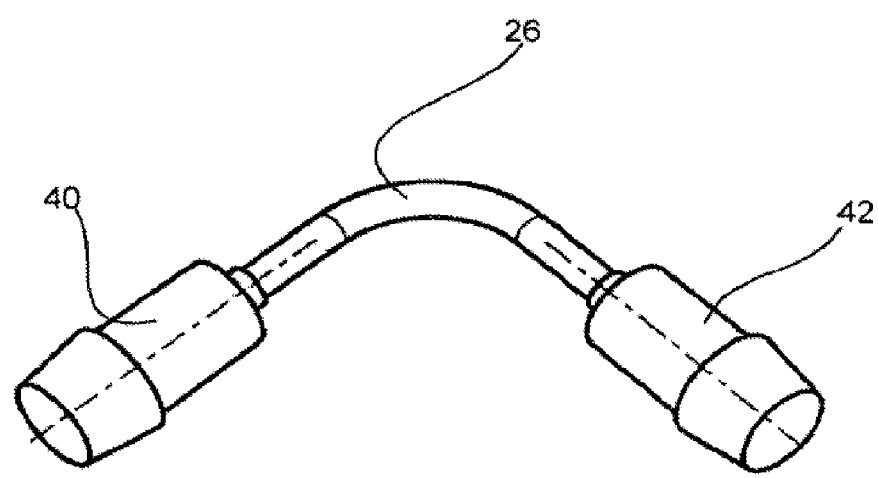
FIG. 4 is a perspective view of the hose of FIG. 3.

The transparent hose 26 is again shown in FIG. 4 with the associated connection elements 40, 42.

Figure 5:
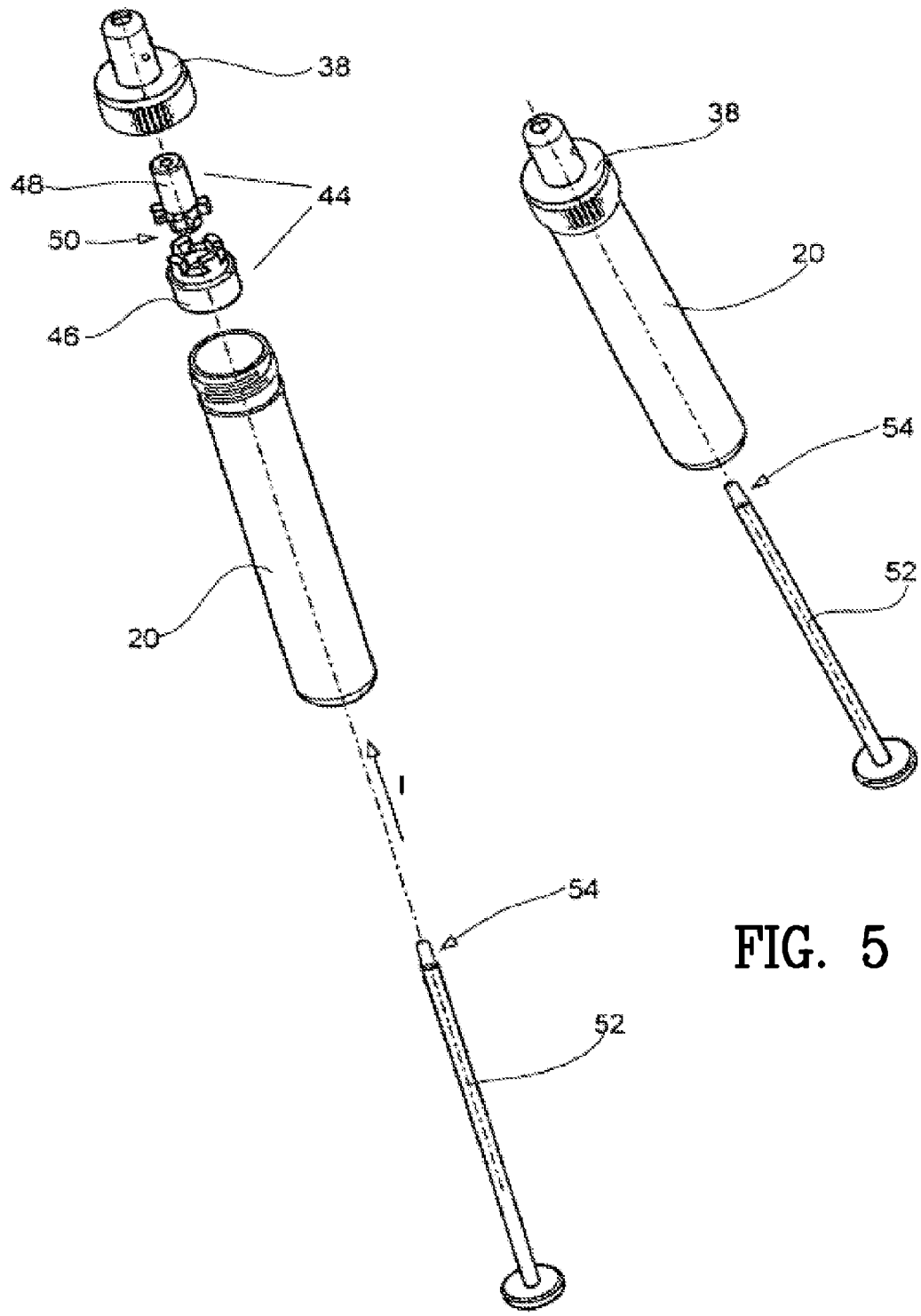
FIG. 5 is a exploded view as well as a view of the assembled status of the secondary tubule.

FIG. 5 shows the secondary tubule 20, 24, once in a mounted and once in a demounted state. As can be taken from the exploded view, the tubule 20, 24 comprises a two-part piston 44.

The two-part piston 44 comprises a backward piston portion 46 as viewed in the screwing-in direction, as well as a forward piston portion 48 which are removably connectable to each other by means of a bayonet coupling 50. Furthermore, the backward piston portion 48 comprises a through bore closed by a seal. Furthermore, a piston rod which has an outer thread 54 in its forward area, is associated with the secondary tubule 20 or 24, respectively.

It is ensured thereby that, after finishing the centrifugation and after removal of the secondary tubules 20, 24 out of the centrifuge, a mixing of the blood component contained in the secondary tubule 20, 24 may be carried out. For this purpose, the piston rod 52 is inserted into the secondary tubule 22, 24, and it is pushed through the through bore contained in the backward piston portion 46 and is subsequently screwed into the forward piston portion 48. After the connection between the piston rod 52 and the forward piston element 48 has been made, the bayonet coupling 50 is disconnected by a further rotation, and the forward piston portion 48 is separated from the backward piston portion 46. By means of an upwards and downwards movement of the forward piston portion 48 with respect to the backward piston portion 46, the blood component contained therein, is manually mixed with the optionally present biocompatible material. After the mixing procedure, the forward piston portion 48 is retracted by means of the piston rod 52 and again fixed to the backward piston portion 46.

With the centrifuge 10, the production of a highly enriched thrombocyte concentrate out of whole blood or a paste out of biocompatible material and thrombocyte concentrate is possible in an advantageous way.

For this purpose, a first tubule 18 filled with whole blood as well as a secondary tubule 20 which optionally contains the biocompatible material, are inserted into the first container receptacle pair 14. A tubule 22 filled with whole blood and having the same weight, and its associated secondary tubule 24 also optionally containing a biocompatible material, are inserted into the second container receptacle pair 16.

Because of the hose detection sensor, a not inserted second container pair and, thereby, an unbalance, would be detected early in time.

After the tubules 18, 20 as well as 22, 24 have been inserted, a start-up of the centrifuge 10 is effected. The first centrifugation process lasts until the erythrocyte concentrate with high density as well as thrombocyte enriched blood plasma separated there from by a separation layer have been formed in the tubules 18, 22.

Subsequently, the speed of the centrifuge 10 is reduced, and the motor/gear units 30a, 32a associated with the tubule 18 and the tubule 22, respectively, are started up and move by means of the associated push rods the piston contained in the tubules 18, 22. This means that a squeezing-off of the thrombocyte enriched blood plasma is effected through the transparent hose 26, 28 into the associated secondary tubules 20, 24 which, as already stated, optionally contains a biocompatible material. The squeezing-off process lasts until the separation layer is detected in the transparent hose 26, 28 by the associated sensor.

Subsequently, the speed of the centrifuge 10 is put up again and a second centrifugation process is effected. The second centrifugation process lasts until a thrombocyte concentrate with higher density as well as thrombocyte depleted blood plasma has been formed in the secondary tubules 22, 24.

Subsequently, the speed is reduced again, and the motor/gear units 30b, 32b associated with the secondary tubule 22, 24 are starting to move. A squeezing-off of a pre-defined volume element out of the secondary tubule 22, 24 follows through the hose 26, 28 into the tubules 18, 20 such that a highly enriched thrombocyte concentrate remains in the secondary tubules 22, 24.

After breaking down the centrifuge and after slowing down the motor/gear units 30a, 30b, 32a and 32b, the tubules 18, 20, 22, 24 can be subsequently removed.

In a further processing step, a piston rod 52 is inserted optionally into each of the secondary tubules 20, 24. By fixing of the piston rod 52 at the forward piston portion 48 and loosening of the bayonet coupling 50 in the above described manner, a mixing of the highly enriched thrombocyte concentrate contained in the secondary tubules with the optionally already provided biocompatible material out into a homogenous paste is carried.

Subsequently, the removal of the highly enriched thrombocyte concentrate or the paste, respectively, out of the secondary tubules 20, 24 is effected by the squeezing-off process.

LIST OF REFERENCE SIGNS 10 centrifuge
11 centrifuge head
12 rotor
14a container receptacle
14b container receptacle
16a container receptacle
16b container receptacle
14 first container receptacle pair
16 second container receptacle pair
18 container/tubule
20 container/secondary tubule
22 container/tubule
24 container/secondary tubule
26 transparent hose
28 transparent hose
30a motor/gear unit
30b motor/gear unit
32a motor/gear unit
32b motor/gear unit
34 push rod
36 closure cap
38 closure cap
40 connection element
42 connection element
44 two-part piston
46 backward piston portion
48 forward piston portion
50 bayonet coupling
52 piston rod
54 outer thread
I insertion direction Those skilled in the art will recognize that the invention has been set forth by way of example herein and that changes may be made to the invention without departing from the spirit and scope of the claims set forth hereinafter.

The invention claimed is:

1. A centrifuge for separating whole blood into blood components, comprising:
a closed-loop control unit and/or an open-loop control unit;
a drive unit coupled to said closed-loop control unit and/or said open-loop control unit for driving said centrifuge;
a first container, a second container, a third container and a fourth container;
a rotor; said rotor includes a first container receptacle, a second container receptacle, a third container receptacle and a fourth container receptacle;
said first container removably resides in said first container receptacle, said second container removably resides in said second container receptacle, said third container removably resides in said third container receptacle and said fourth container removably resides in said fourth container receptacle;
said first and second containers being in fluid communication with each other;
said third and fourth containers being in fluid communication with each other;
a first transfer means operationally connected with said first container, a second transfer means operationally connected with said second container, a third transfer means operationally connected with said third container, and a fourth transfer means operationally connected with said fourth container;
said first, second, third and fourth transfer means coupled to said closed-loop control unit and/or said open-loop control unit;
said first, second, third, and fourth transfer means include first, second, third and fourth motor/gear units, respectively;
said first and second transfer means and said first and said second containers transfer and back transfer blood components between said first and second containers;
said third and fourth transfer means and said third and said fourth containers transfer and back transfer blood components between said third and fourth containers;
a first sensor resides between said first and said second container receptacles and detects a separation layer of said blood components, said first sensor is coupled to said closed-loop control unit and/or said open-loop control unit; and, a second sensor resides between said third and said fourth container receptacles and detects a separation layer of said blood components, said second sensor is coupled to said closed-loop control unit and/or said open-loop control unit.

2. Centrifuge according to claim 1, wherein: in at least one tubule, said piston includes a backward piston portion and a forward piston portion, said forward and backward piston portions are removably connected to each other; and, said backward piston portion comprises a through hole tightly sealed such that, after disconnecting said two piston portions, said forward piston portion is movable relative to said backward piston portion by means of a piston rod inserted through said through hole in said backward piston portion.

3. Centrifuge according to claim 2, wherein said backward piston portion and said forward piston portion are removably connected to each other by means of a bayonet coupling, and said forward piston portion comprises a bore with an interior thread and said piston rod comprises an outer thread.

4. Centrifuge according to claim 1, wherein two tubules are connected to each other in fluid communication by means of a transparent hose.

5. Centrifuge according to claim 4, wherein said hose includes connection elements and said tubules include closure caps, said connection elements being removably connected to said closure caps of said tubules.

* * * * *

UNITED STATES PATENT AND TRADEMARK OFFICE
CERTIFICATE OF CORRECTION

PATENT NO. : 8,951,180 B2
APPLICATION NO. : 12/875399
DATED : February 10, 2015
INVENTOR(S) : Eberle Page 1 of 1

It is certified that error appears in the above-identified patent and that said Letters Patent is hereby corrected as shown below:

In the Claims

Col. 9, line 3, claim 1, after "unit;" delete "and,".

Col. 9, line 8, claim 1, after "...unit" delete "." and insert -- ; and, said containers form a closed system for the sterile processing of blood samples, said containers are tubules, said transfer means associated with each of said tubules includes a movable piston residing therein, respective push rods associated with each of said tubules removably engage said respective pistons, and said respective push rods being operationally connected to said respective motor/gear units. --.

Signed and Sealed this
Twenty-sixth Day of May, 2015

Michelle K. Lee
*Director of the United States Patent and Trademark Office*